US005767058A

United States Patent [19]
Watanabe et al.

[11] Patent Number: 5,767,058
[45] Date of Patent: Jun. 16, 1998

[54] DETERGENT COMPOSITION

[75] Inventors: Yuko Watanabe, Tokyo; Riho Honjo, Kanagawa; Hiroshi Kuzui, Tokyo; Toru Tagawa, Kanagawa, all of Japan

[73] Assignee: Mitsubishi Chemical Corporation, Tokyo, Japan

[21] Appl. No.: 736,956

[22] Filed: Oct. 25, 1996

[30] Foreign Application Priority Data

Oct. 26, 1995 [JP] Japan ................... 7-300433

[51] Int. Cl.$^6$ .................. C11D 1/831; C11D 9/32
[52] U.S. Cl. ............. 510/470; 510/119; 510/137; 510/138
[58] Field of Search ............. 510/470, 119, 510/137, 138

[56] References Cited

U.S. PATENT DOCUMENTS 2,733,252  1/1956  Thompson et al.
4,029,606  6/1977  Isa et al. ................. 510/111 X
4,846,991  7/1989  Suzue et al. ............. 510/119 X
5,047,165  9/1991  Lysy et al. ............... 510/470 X

OTHER PUBLICATIONS

Thewlis, Basil H., "The Fate of Stearoyl Lactylates When Used in Breadmaking", J. Sci. Food Agric. 1981, 32 125–128, Jun. 16, 1980.

Primary Examiner—Michael Lusignan
Attorney, Agent, or Firm—Sughrue, Mion, Zinn, Macpeak & Seas, PLLC

[57] ABSTRACT

A detergent composition comprising a sucrose fatty acid ester and a salt of long-chain carboxylic acid ester of lactic acid having a purity of at least 80 mol %. The detergent composition is highly safe, is weak acidic or neutral so that it has low irritation to the skin, is excellent in detergent properties such as detergency, foaming power and stability in hard water and also in feeling upon use, and is free from undesired color or odor, so that it is suited particularly as food and dish detergents, and skin and hair detergents such as shampoo, body shampoo, face wash and hand soap.

17 Claims, No Drawings

DETERGENT COMPOSITION

FIELD OF THE INVENTION

The present invention relates to a detergent composition. In particular, the present invention relates to a detergent composition which is free from irritation to the skin and hair and is excellent in foaming power, detergency, feeling upon use and external appearance at the time of storage.

BACKGROUND OF THE INVENTION

As detergent compositions used by making contact with the skin or hair of the human body or detergents for washing the materials which contact with the mucosae or skin of the human body, shampoo, body shampoo, face wash, shaving foam, food and dish detergent and the like have been known to date. These detergents are requested to contain a surfactant which has good surface activating capacities such as surface tension, emulsifying power, solubilizing power and foaming power but also is safe and has low irritation to the skin. However, the current situation is that the conventional detergents do not always satisfy such requirements fully. For example, an alkali metal salt of a fatty acid (i.e., soap) is not preferred because upon use, it dissociates into the fatty acid and a hydroxide of the alkali metal in the presence of water so that it becomes alkaline-and roughens the skin. Synthetic anionic surfactants such as sodium alkylbenzenesulfonate have strong detergency but are not always harmless to the body and environment. On the other hand, the single use of the nonionic surfactant such as polyoxyethylene alkyl ether has a moderate influence on the skin but often insufficient in detergency and foaming power. There is accordingly a demand for the development of detergents which are safe, have low irritation to the skin and have excellent detergency.

It is known that salts of long-chain carboxylic acid ester of lactic acid are anionic surfactants and are useful as emulsifiers for food or cosmetics, and surfactants constituting detergents, etc. (JP-A-49-73404, JP-A-54-13471, JP-A-64-6237 and JP-A-4-23900) (the term "JP-A" as used herein means an "unexamined published Japanese patent application"). In the above cases, however, they are used in a comparatively small amount as assistant surfactants for cosmetics or detergents, or conditioners for controlling the touch feeling of the skin or hair after washing, together with another surfactant. for those purposes, only the reaction products which still contain a fatty acid and the like which are the raw materials for preparing the above lactic ester salt are used.

That is, the salt of long-chain carboxylic acid ester of lactic acid has so far been prepared by reacting a long-chain carboxylic acid or a reactive derivative such as a long-chain carboxylic acid chloride with a lactic acid to prepare a long-chain carboxylate lactic ester and then, reacting the resulting ester with a basic substance or with a lactic salt directly. The reaction mixture so obtained is provided for use in various applications without any treatment. The reason may be that an industrially applicable method for purifying a salt of long-chain carboxylic acid ester of lactic acid has not been known and besides, an influence of the coexisting substances on the salt of long-chain carboxylic acid ester of lactic acid has not been elucidated sufficiently. However, an aqueous solution of the reaction mixture containing such a salt of long-chain carboxylic acid ester of lactic acid is accompanied with the problem that it has a higher Krafft point and is insufficient in detergency and foaming power compared with an aqueous solution of a highly purified salt of long-chain carboxylic acid ester of lactic acid. The Krafft point is a factor having an influence on the surface activating capacities of a surfactant. At the temperatures lower than the Krafft point, surface activating capacities such as detergency, foaming power and emulsifying power cannot be exhibited fully so that an increase in the Krafft point which leads to the lowering in the surface activating capacities is not preferred.

The reaction mixture is also accompanied with a problem that it is often colored and has a caramel odor and therefore has an unfavorable influence on the external appearance and odor of the aqueous solution of the reaction mixture or products using the same.

On the other hand, the sucrose fatty acid ester is a nonionic surfactant and known to have useful effects for emulsification of food, cosmetics or the like or modification of the oils and fats (JP-A-5-219885, JP-A-6-271420 and JP-A-6-153798).

This surfactant has remarkably high safety, has a moderate influence on the skin and has good biodegradability, but, when used singly as a detergent, it is not satisfactory in view of the detergency and foaming power.

An object of the present invention is to provide a detergent composition which is weakly acidic or neutral, has low irritation to the skin or hair, has excellent detergent properties such as foaming power, detergency and stability in hard water and excellent feeling upon use with favorable external appearance without coloring or odor.

SUMMARY OF THE INVENTION

The present inventors have conducted an extensive studies with a view to attaining the above object. As a result, it was found that a detergent composition having excellent detergent properties, safety, and favorable feeling upon use can be obtained by using in combination a salt of long-chain carboxylic acid ester of lactic acid having a specific purity, that is a purity of at least 80 mol %, preferably at least 90 mol %, more preferably at least 95 mol %, and a sucrose fatty acid ester, thus resulting in the completion of the present invention.

Thus, the gist of the present invention resides in a detergent composition comprising a salt of long-chain carboxylic acid ester of lactic acid having a purity of at least 80 mol % and a sucrose fatty acid ester.

DETAILED DESCRIPTION OF THE INVENTION

Hereinafter, the present invention is described in detail.

As the long-chain carboxylic acid in the salt of long-chain carboxylic acid ester of lactic acid used in the present invention, a carboxylic acid having at least 8 carbon atoms, more specifically, generally 8–20, preferably 10–18, more preferably 10–14 carbon atoms, in the direction of the long chain can be used (inclusive of the carbon atom of the carboxylic group). The long-chain carboxylic acid may be saturated or unsaturated, or in the linear or branched chain form. In the case of the branched chain carboxylic acid, the longest chain preferably has at least 8 carbon atoms. In some cases, hydroxycarboxylic acid having an hydroxyl group can be used. Examples of the long-chain carboxylic acid include caprylic acid, capric acid, lauric acid, myristic acid, palmitic acid, stearic acid, arachic acid, oleic acid, elaidic acid, ricinoleic acid, 2-butyloctanoic acid, 2-hexyldecanoic acid, 2-hexylundecanoic acid, 2-octyldecanoic acid, 10-hydroxyoctadecanoic acid and 2-hydroxydecanoic acid, and the like. Of these, capric acid, lauric acid and myristic acid are particularly preferred from the viewpoint of detergency. These long-chain carboxylic acids may be used in combination or two or more at any ratio.

The salt of long-chain carboxylic acid ester of lactic acid of the present invention is preferably an aliphatic carboxylic acid derivative represented by the formula:

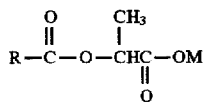

wherein
R represents an aliphatic hydrocarbon group having from 9 to 17 carbon atoms, and
M represents an alkali metal, alkaline earth metal, or an amino group.

As the lactic acid in the salt of long-chain carboxylic acid ester of lactic acid, either one prepared by the fermentation method or synthesis method may be employed. It also embraces both D isomer and L isomer.

The method to prepare a salt of long-chain carboxylic acid ester of lactic acid having a purity of at least 80 mol % is not particularly limited, and any means can be employed.

It is preferred, in general, to purify the reaction product, which is obtained in a known method, by some means.

In general, the reaction between a long-chain carboxylic acid or its reactive derivative (e.g., long-chain carboxylic acid chloride, long-chain carboxylic acid salts, and long-chain carboxylic acid esters) and lactic acid or a lactic salt is carried out at 100° to 250° C. for 2 to 10 hours (for example, U.S. Pat. No. 2,733,252). The reaction can be carried out either in the presence or absence of a basic solvent such as pyridine. Particularly, in the case where a long-chain carboxylic acid chloride is used in a basic solvent, the reaction can be carried out at 50° to 90° C. for 1 to 3 hours.

In the reaction mixture of the above, there exist, in addition to a salt of long-chain carboxylic acid ester of lactic acid, a long-chain carboxylic acid lactic ester, unreacted long-chain carboxylic acid or a salt thereof, lactic acid or a salt thereof, polylactic acid or a salt thereof, and a long-chain carboxylic acid polylactic ester or a salt thereof, and a solvent if it is employed. The reaction mixture is often colored or has somewhat odor. Although the content of the long-chain carboxylic acid lactic ester or a salt thereof in the reaction product except the solvent differs with the ratio of the long-chain carboxylic acid to lactic acid provided for the reaction, but it is generally about 30 to 70 mol % based on the total amount of the long-chain carboxylic acid lactic ester or a salt thereof, unreacted long-chain carboxylic acid or a salt thereof, lactic acid or a salt thereof, polylactic acid or a salt thereof and long-chain carboxylic acid polylactic ester or a salt thereof. The salt of long-chain carboxylic acid ester of lactic acid having a purity of at least 80 mol %, which is to be used in this invention, can be obtained by purifying the esterified reaction mixture in accordance with the usual purification method.

Alternatively, the salt of long-chain carboxylic acid ester of lactic acid having a purity of at least 80 mol % may be formed by preparing a long-chain carboxylate lactic ester having a purity of at least 80 mol % and then forming its salt without leaving the unreacted raw materials.

The long-chain carboxylate lactic ester having a purity of at least 80% can be obtained, for example, by subjecting the reaction mixture to liquid-liquid extraction at pH 5.0 or lower using a water solvent and an organic solvent, thereby forming an organic solvent phase abundant in the long-chain carboxylic acid lactic ester and a water solvent phase abundant in lactic acid, separating these phases each other, and then separating the long-chain carboxylic acid lactic ester in the organic solvent phase from coexisting long-chain carboxylic acid by crystallization; or by adding an aqueous acid solution to the reaction mixture until pH lowers below 3.0, thereby precipitating the long-chain carboxylic acid lactic ester as an oil, collecting the oil, dissolving the resulting oil in an organic solvent and then crystallizing the long-chain carboxylic acid lactic ester from the resulting solution.

More specifically, the long-chain carboxylic acid lactic ester having a purity of at least 80 mol % can be obtained by adding an aqueous solution of hydrochloric acid or sulfuric acid to the reaction mixture so that the total amount (solid content) of the reaction substances, except the solvent, in the resulting aqueous solution becomes 3 to 40% by weight and so that the pH of the resulting aqueous solution becomes 2 to 4, adding an organic solvent, such as hexane or chloroform, which is sparingly insoluble in water and exhibits great dissolving power to the long-chain carboxylic acid lactic ester generally by 0.3 to 2 times the volume of the water phase to conduct liquid-liquid extraction, subjecting the resulting organic solvent to fractional crystallization in a solid content of 5 to 15% by weight to collect the long-chain carboxylic acid lactic ester, and repeating the crystallization operation as needed.

In an aqueous solution or in an alcoholic (such as ethanol) aqueous solution, a basic substance is added to the long-chain carboxylic acid lactic ester so obtained having a purity of at least 80 mol % at a molar ratio of 1:0.9 to 1:1.3 (the long-chain carboxylic acid lactic ester: the basic substance) for reaction, whereby a salt of long-chain carboxylic acid ester of lactic acid having a purity of at least 80 mol % can be obtained.

The more preferred molar ratio of the long-chain carboxylic acid lactic ester to the basic substance is 1:1 to 1:1.2. By maintaining the molar ratio within this range, it is possible to suppress the hydrolysis occurring with the passage of time and suppress an increase in the Krafft point, in other words, to suppress the deterioration in the surface activating capacities. When the molar ratio of the basic substance is large, the Krafft point of the aqueous solution of the salt of long-chain carboxylic acid ester of lactic acid increases, leading to the deterioration in transparency or the formation of a heterogeneous condition at ordinary temperature owing to the precipitation of the long-chain carboxylic acid metal salt (soap). This phenomenon is considered to occur because an increase in the basic substance accelerates the hydrolysis of the long-chain carboxylic acid lactic ester so that the ratio of the salt of long-chain carboxylic acid ester of lactic acid decreases while the ratios of the soap and lactic acid show an increase.

When the molar ratio of the basic substance is too small, on the other hand, the Krafft point of the aqueous solution also increases. Although the hydrolysis ratio of the long-chain carboxylic acid lactic ester is low, the surface activating capacities is low owing to a small amount of the basic ion, so that it is considered that even if the amounts of the long-chain carboxylic acid and lactic acid formed by the hydrolysis are small, not only the Krafft point increases but also surface activating capacities such as emulsifying power, foaming power and detergency decrease.

A detergent containing the salt of long-chain carboxylic acid ester of lactic acid exhibits excellent properties in a neutral pH range by employing as the salt a highly purified salt of long-chain carboxylic acid ester of lactic acid which has been neutralized at a predetermined molar ratio. Illustrative of the basic substance include hydroxides or carbonates of an alkali metal or alkaline earth metal, ammonia, alkanolamines such as ethanolamine and lower alkylamines such as tributylamine. Of these, potassium, sodium, triethanolamine salts are preferred as the basic substance used for detergents because they are free from irritation to the skin, and show a low Krafft point and have excellent detergency and foaming power.

With respect to the sucrose fatty acid ester used in the present invention, a fatty acid having 8 to 24 carbon atoms, preferably 10 to 18 carbon atoms, more preferably 10 to 14 carbon atoms may be employed. The fatty acid may be saturated or unsaturated. In some cases, hydroxycarboxylic acid containing one or more hydroxyl groups can also be used. Examples of the fatty acid include caprylic acid, capric acid, lauric acid, myristic acid, palmitic acid, stearic acid, arachic acid, oleic acid, elaidic acid, and ricinoleic acid. Of these, capric acid, lauric acid and myristic acid are particularly excellent and therefore are preferred. These fatty acids may also be used in combination of two or more at any proportion. From the industrial viewpoint, it is suited to use mixed fatty acid available from coconut oil, palm oil, beef tallow or the like as a raw material for preparation. Of the sucrose fatty acid esters composed of such a fatty acid, those containing mono- and di-esters in a total amount of at least 80% by weight or those having an HLB value of at least 9 are more preferred. When the total amount of the monoester and diester is small and that of the triester and higher esters is large, there are cases where the sucrose fatty acid ester has low water solubility, leading to the lowering in the detergent properties.

The salt of long-chain carboxylic acid ester of lactic acid and sucrose fatty acid ester used in the detergent composition according to the present invention are generally contained in an amount of from 1 to 90% by weight, preferably 5 to 60% by weight, and more preferably 5 to 50% by weight, each based on the total amount of the detergent.

The salt of long-chain carboxylic acid ester of lactic acid and the sucrose fatty acid ester are contained in a weight ratio falling within a range of 90:10 to 6:94, preferably 80:20 to 10:90, more preferably 60:40 to 40:60. When the weight ratio of the salt of long-chain carboxylic acid ester of lactic acid to the sucrose fatty acid ester is outside the above range, there are the cases where the resulting detergent has insufficient foaming power and can provide neither sufficiently fine-textured foams nor the favorable touch feeling to the skin or hair after washing.

The detergent composition according to the present invention may optionally contain a chelating agent in order to show the detergency sufficiently. The use of the chelating agent makes it possible to avoid turbidity of the hard water solution caused by the formation of scales in the hard water containing calcium, magnesium or the like but also to maintain the detergency, foaming power and touch feeling of foams in the hard water.

Such a chelating agent is not particularly limited and the conventionally used chelating agents may be employed. Specific examples include citrates, malates, tartrate, glutamates, pyrrolinates, polyacrylates, polymaleates, gluconates, nitrilotriacetates, salts of an acrylic acid-maleic anhydride copolymer, salts of a maleic anhydride-methyl vinyl ether copolymer, salts of a maleic anhydride-olefin copolymer, salts of a maleic anhydride-methacrylic acid copolymer, maleic anhydride-tartaric acid condensate, zeolite, tripolyphosphates, ethylenediaminetetraacetate (EDTA) and ethylenediamine.

Of these, citrates, malates, tartrate, glutamates, pyrrolinates, and the like are used preferably because they are highly safe to the human body, free from environmental pollution, highly compatible with the salt of long-chain carboxylic acid ester of lactic acid and sucrose fatty acid ester which are used together and, in addition, with water and alcohol which constitute the detergent, and excellent in detergency, stain dispersibility, foaming power and touch feeling of foams. One or more chelating agents selected from the above group in an amount of 0.01 to 50% by weight, preferably 1 to 30% by weight may be contained based on the total weight of the detergent composition of the present invention.

It is also possible to add, to the detergent composition of the present invention, any components conventionally used for the detergent for general use within an extent not impairing the object of the present invention. Examples of such additional components include surfactants which have a moderate influence on the human body, such as sodium polyoxyethylene alkyl ether sulfonate, polyoxyethylene alkyl ether, polyoxyethylene alkyl phenyl ether, polyglycerine fatty acid ester, monoglyceride, organic acid monoglyceride, sorbitan fatty acid ester, polyoxyethylene sorbitan fatty acid ester, fatty acid alkanol amide, carboxybetaine-type surfactant, imidazolinium-type surfactant, sulfobetaine-type surfactant and aminoacid-type surfactants; inorganic builders such as sodium carbonate, sodium sulfate, sodium chloride, magnesium sulfate and calcium chloride; fluidity improvers such as glycerin, ethanol, propylene glycol and polyethylene glycol; thickeners such as carboxymethyl cellulose and hydroxyethyl cellulose; perfumes, colorants, moisturizing agents, sterilizers, enzymes and anti-inflammatory agents.

The detergent composition according to the present invention may be employed as various detergents which have many opportunities to make contact with the skin, for example, detergents for skin or hair, and those for foods, dishes or kitchen tools. These detergents may be supplied in any one of the liquid, paste and solid forms.

In general, the detergent is used in the form of liquid or paste after diluting it with a solvent. Since the detergent is used in an aqueous system and frequently contacts with the skin, the solvent is preferably an aqueous solvent which can be mixed with water easily and shows only low irritation to the skin. Examples of the solvent include water and hydrophilic solvents which can be mixed with water easily and show low irritation to the skin. Examples of the hydrophilic solvents include alcohols, particularly, ethanol.

The detergent composition according to the present invention is highly safe, is weak acidic or neutral so that it has low irritation to the skin, is excellent in detergent properties such as detergency, foaming power and stability in hard water and also in feeling upon use, and is free from undesired color or odor, so that it is suited particularly as food and dish detergents, and skin and hair detergents such as shampoo, body shampoo, face wash and hand soap.

The present invention will hereinafter be described in more specifically. It should however be borne in mind that the present invention is not limited to or by the following examples so long as they do not depart from the subject matter.

EXAMPLES 1 to 11 AND COMPARATIVE
EXAMPLES 1 to 6

In each example, a liquid detergent was prepared using a salt of long-chain carboxylic acid ester of lactic acid and a sucrose fatty acid esters at a weight ratio shown in Table 1. The results of the evaluation of its function are also shown in Table 1.

Incidentally, high-purity and low-purity salts of lauric acid ester of lactic acid were prepared using as a raw material a salt of lauric acid ester of lactic acid obtained in a known manner.

The lauric acid ester of lactic acid was prepared in accordance with a known preparation example, i.e., by reacting 120 g of lauric acid, 72 g of lactic acid (purity: 90%) and 25 g of potassium carbonate at 200° C. under a nitrogen stream for 5 hours. The laurate lactic ester so obtained contains a lauric acid lactic ester and lauric acid dilactic ester in a total amount of 61 mol %, 30 mol % of lauric acid, lactic acid and a lactic acid polymer.

The high-purity potassium salt of lauric acid ester of lactic acid having a purity of 99 mol % or higher is obtained by subjecting the lauric acid lactic ester obtained in a known manner to liquid-liquid extraction and then crystallization to obtain a lauric acid lactic ester having a purity of 99 mol % or higher, and then neutralizing the lauric acid lactic acid with an equivalent amount of potassium hydroxide. The low-purity potassium salt of lauric acid ester of lactic ester used in Comparative Example was prepared using as a raw material the lauric acid lactic ester obtained in a known manner and its purity was 44 mol %.

The sucrose fatty acid ester employed contains lauric acid as the fatty acid and the total of the monoester and diester amounts to at least 95% by weight of the total weight.

A high-purity potassium salt of myristic acid ester of lactic acid having a purity of 99 mol % or higher used in Example 8 was prepared in the same manner as described above except that the fatty acid was changed to myristic acid. The reaction product and purified product of this salt of long-chain carboxylic acid ester of lactic acid are the same with those of the $C_{12}$ product (more than 99%). A high-purity potassium salt of lauric acid ester of lactic acid having a purity of 99 mol % or higher used in Example 9 was prepared in the same manner as described above except that the molar ratio of the long-chain carboxylic acid lactic ester/the basic substance at the time of neutralization was changed to 1:1.2. The purified product of this salt of long-chain carboxylic acid ester of lactic acid is the same with that of 1/1 product (more than 99%). In addition, a sucrose fatty acid ester of which fatty acid moiety was derived from myristic acid and the total weight ratio of monoester and diester is 95% by weight or more was used in Example 8.

The detergent was evaluated as follows:

1. External appearance: the external appearance of the undiluted detergent liquid at 25° C. was observed under natural light.

o: Colorless and transparent

Δ: Slightly turbid or slightly colored x: Turbid or brown color

2. Odor: the odor of the undiluted detergent liquid at 25° C. were evaluated.

o: Odorless

Δ: Slight caramel odor x: Strong caramel odor

3. Foaming power: in a 50 ml graduated test tube, 10 ml of an aqueous solution of the detergent (a 0.1% by weight solution in tap water) were charged, followed by the addition of 2.5 mg of commercially available soybean salad oil. The resulting mixture was agitated up and down for one minute at 25° C. at 200 times/minute and the resulting mixture was allowed to stand for 30 seconds. Then, the volume of the foams was measured.

4. Stability in hard water: based on the presence or absence of the turbidity of an aqueous solution of the detergent (a 0.25% by weight solution in tap water), evaluation was carried put.

o: Colorless and transparent

Δ: Slightly turbid x: Turbid 5. pH: the pH of the undiluted detergent liquid at 25° C. was measured.

6. Feeling of hands at the time of or after use: On the hands wetted with tap water, 0.5 ml of the detergent was placed and washing was conducted for one minute by rubbing the hands. The fineness of the texture of the foams was visually evaluated. One minute later, the hands were rinsed with running water for 15 seconds. The water on the hands was sufficiently wiped off with a dry towel and then, the hands were allowed to stand still. Presence or absence of dry feeling or a unpleasant feeling of the skin of the hands and presence or absence of the unpleasant feeling of disorder such as the stretched feeling of the skin of the hands were evaluated during 60 minutes. Incidentally, the measurement was carried out under the conditions at 25° C. both in the temperature and the water temperature.

Fineness of the texture of foams at the time of washing:

o: finely-textured and creamy foams

Δ: slightly rough foams x: rough and dry foams

Dry feeling:

o: not dry but moisturized feeling of the hand skin

Δ: slight dry feeling of the hand skin x: dry feeling of the hand skin

Unpleasant feeling:

o: no stretched feeling or irritation to the hand skin and mild touch

Δ: slight stretched feeling or irritation to the hand skin x: stretched feeling or irritation to the hand skin.

As a result of the function evaluation test, the liquid detergent containing a high-purity salt of long-chain carboxylic acid ester of lactic acid having a purity of at least 80 mol %, a sucrose fatty acid ester and a chelating agent is colorless and odorless, has excellent foaming power, has finely-textured foams, and preferable feeling upon use which is not available in the detergent of a single composition.

Such characteristics can be found in the combination of a sucrose fatty acid ester (SE) and a high-purity salt of long-chain carboxylic acid ester of lactic acid. Even if the surfactant is similarly anionic, the combination of SE and a soap showed that the resultant foams had no fine texture and no preferable feeling upon use. The liquid detergent containing unpurified salt of long-chain carboxylic acid ester of lactic acid prepared in a known manner, that is, the detergent containing a salt of long-chain carboxylic acid ester of lactic acid having a purity less than 80 mol %, had brown color and caramel odor and were inferior to the detergent using a salt of long-chain carboxylic acid ester of lactic acid having a purity of at least 80 mol % in all the points of foaming power, fineness of the texture of the foams and feeling upon use.

TABLE 1

Composition of detergent and evalution results

| | \multicolumn{10}{c}{Example} | | | | | | | | | |
|---|---|---|---|---|---|---|---|---|---|---|
| | 1 | 2 | 3 | 4 | 5 | 6 | 7 | 8 | 9 | 10 |
| Composition (% by weight) | | | | | | | | | | |
| High-purity potassium salt of lauric acid ester of lactic acid | 18 | 16 | 12 | 8 | 4 | 2 | 1.2 | 8 | 8 | 8 |
| Low-purity potassium salt of lauric acid ester of lactic acid | — | — | — | — | — | — | — | — | — | — |
| Potassium laurate (soap) | — | — | — | — | — | — | — | — | — | — |
| Sucrose fatty acid ester | 2 | 4 | 8 | 12 | 16 | 18 | 18.8 | 12 | 12 | 12 |
| Sodium citrate | 15 | 15 | 15 | 15 | 15 | 15 | 15 | 15 | 15 | 30 |
| Ethanol | 5 | 5 | 5 | 5 | 5 | 5 | 5 | 5 | 5 | 5 |
| Desalted water | Balance | Balance | Balance | Balance | Balance | Balance | Balance | Balance | Balance | Balance |
| Evaluation Results | | | | | | | | | | |
| External appearance | ○ | ○ | ○ | ○ | ○ | ○ | ○ | ○ | ○ | ○ |
| Odor | ○ | ○ | ○ | ○ | ○ | ○ | ○ | ○ | ○ | ○ |
| pH | 6.2 | 6.2 | 6.2 | 6.2 | 6.2 | 6.2 | 6.2 | 6.0 | 6.3 | 6.2 |
| Fineness of the texture of foams at the time of washing | ○ | ○ | ○ | ○ | ○ | ○ | ○ | ○ | ○ | ○ |
| Dry feeling after washing | ○ | ○ | ○ | ○ | ○ | ○ | ○ | ○ | ○ | ○ |
| Unpleasant feeling after washing | Δ | ○ | ○ | ○ | ○ | ○ | ○ | ○ | ○ | Δ |
| Foaming power/ml | 3 | 3 | 22 | 22 | 12 | 12 | 12 | 5 | 22 | 22 |
| Stability in hard water | ○ | ○ | ○ | ○ | ○ | ○ | ○ | ○ | ○ | ○ |
| Salt of long-chain carboxylic acid ester of lactic acid/ sucrose fatty acid ester | 90/10 | 80/20 | 60/40 | 40/60 | 20/80 | 10/90 | 6/94 | 40/60 | 40/60 | 40/60 |

| | Example | | | Comparative Example | | | | | |
|---|---|---|---|---|---|---|---|---|---|
| | 11 | 12 | 13 | 1 | 2 | 3 | 4 | 5 | 6 |
| Composition (% by weight) | | | | | | | | | |
| High-purity potassium salt of lauric acid ester of lactic acid | 12 | 4 | 16 | — | 20 | — | — | — | — |
| Low-purity potassium salt of lauric acid ester of lactic acid | — | — | — | — | — | 12 | 8 | — | — |
| Potassium laurate (soap) | — | — | — | — | — | — | — | 12 | 8 |
| Sucrose fatty acid ester | 8 | 6 | 24 | 20 | — | 8 | 12 | 8 | 12 |
| Sodium citrate | — | 15 | 5 | 15 | 15 | 15 | 15 | 15 | 15 |
| Ethanol | 5 | 5 | 5 | 5 | 5 | 5 | 5 | 5 | 5 |
| Desalted water | Balance | Balance | Balance | Balance | Balance | Balance | Balance | Balance | Balance |
| Evaluation Results | | | | | | | | | |
| External appearance | ○ | ○ | ○ | ○ | ○ | X | X | ○ | ○ |
| Odor | ○ | ○ | ○ | ○ | ○ | X | X | ○ | ○ |
| pH | 6.3 | 6.2 | 6.2 | 6.3 | 6.3 | 6.1 | 6.2 | 8.0 | 8.1 |
| Fineness of the textural of foams at the time of washing | ○ | ○ | ○ | X | ○ | X | X | Δ | X |
| Dry feeling after washing | ○ | ○ | ○ | Δ | ○ | ○ | Δ | X | X |
| Unpleasant feeling after washing | ○ | ○ | ○ | ○ | Δ | ○ | ○ | X | X |
| Foaming power/ml | 10 | 13 | 22 | 4 | 0 | 8 | 17 | 0 | 0 |
| Stability in hard water | X | ○ | ○ | ○ | ○ | ○ | ○ | X | X |
| Salt of long-chain carboxylic acid ester of lactic acid/ sucrose fatty acid ester | 60/40 | 40/60 | 40/60 | 0/100 | 100/0 | 60/40 | 40/60 | — | — |

While the invention has been described in detail and with reference to specific embodiments thereof, it will be apparent to one skilled in the art that various changes and modifications can be made therein without departing from the spirit and scope thereof.

What is claimed is:

1. A detergent composition comprising a sucrose fatty acid ester and a salt of a long chain carboxylic acid ester of lactic acid, said salt of said long-chain carboxylic acid ester of lactic acid having a purity of at least 80% wherein a total amount of the sucrose fatty acid ester and the salt of the long-chain carboxylic acid ester of lactic acid is from 1 to 90% by weight based on the total amount of the detergent, wherein a weight ratio of the salt of the long-chain carboxylic acid ester of lactic acid and the sucrose fatty acid ester is within the range of from 90:10 to 6:94, wherein the number of carbon atoms of the fatty acid moiety of the sucrose fatty acid ester is 8 to 24 and wherein the number of carbon atoms of the long-chain carboxylic acid moiety of the salt of the long-chain carboxylic acid ester of lactic acid is 8 to 20.

2. The detergent composition according to claim 1, wherein the sucrose fatty acid ester contains lauric acid as the fatty acid and the total of monoester and diester amounts to at least 95% by weight of the total weight of the sucrose fatty acid ester and wherein the salt of a long-chain carboxylic acid ester of lactic acid is a potassium salt of lauric acid ester of lactic acid.

3. The detergent composition according to claim 1, wherein a total amount of the sucrose fatty acid ester and the salt of long-chain carboxylic acid ester of lactic acid is from 5 to 60% by weight based on the total amount of the detergent.

4. The detergent composition according to claim 1, wherein a total amount of the sucrose fatty acid ester and the salt of long-chain carboxylic acid ester of lactic acid is from 5 to 50% by weight based on the total amount of the detergent.

5. The detergent composition according to claim 1, which further comprises an aqueous solvent.

6. The detergent composition according to claim 5, wherein said aqueous solvent is a hydrophilic solvent.

7. The detergent composition according to claim 6, wherein said hydrophilic solvent is an alcohol.

8. The detergent composition according to claim 6, wherein said alcohol is ethanol.

9. The detergent composition according to claim 1, which further comprises a chelating agent in an amount of from 0.01 to 50% by weight based on the total weight of the detergent.

10. The detergent composition according to claim 1, wherein a weight ratio of the salt of long-chain carboxylic acid ester of lactic acid and the sucrose fatty acid ester is within a range of from 80:20 to 10:90.

11. The detergent composition according to claim 1, wherein a weight ratio of the salt of long-chain carboxylic acid ester of lactic acid and the sucrose fatty acid ester is within a range of from 60:40 to 40:60.

12. The detergent composition according to claim 1, wherein the salt of long-chain carboxylic acid ester of lactic acid is a reaction product of the carboxylic acid represented by the formula:

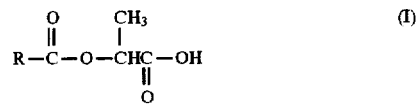

wherein R represents an aliphatic hydrocarbon group having 9 to 17 carbon atoms, and a basic substance.

13. The detergent composition according to claim 12, wherein the salt of long-chain carboxylic acid ester of lactic acid is a reaction product of the carboxylic acid compound represented by the formula (I) and the basic compound at a molar ratio of from 1:0.9 to 1:1.3.

14. The detergent composition according to claim 12, wherein the salt of long-chain carboxylic acid ester of lactic acid is a reaction product of the carboxylic acid represented by the formula (I) and the basic compound at a molar ratio of from 1:1 to 1:1.2.

15. The detergent composition according to claim 1, which further comprises a chelating agent.

16. The detergent composition according to claim 1, which further comprises a chelating agent in an amount of from 1 to 30% by weight based on the total weight of the detergent.

17. The detergent composition according to claim 15, wherein said chelating agent is selected from the group consisting of citrates, malates, tartrate, glutamates, and pyrrolinates.

* * * * *

UNITED STATES PATENT AND TRADEMARK OFFICE
CERTIFICATE OF CORRECTION

Page 1 of 6

PATENT NO. : 5,767,058
DATED : June 16, 1998
INVENTOR(S) : Watanabe, Yuko, et. al.

It is certified that error appears in the above-identified patent and that said Letters Patent is hereby corrected as shown below:

Column 1, line 14, delete "the" (first occurrence);

Column 1, line 17, delete "are requested to";

Column 1, line 20, after "but" insert --must--, after "also" delete "is" and insert --be--, and delete "has" and insert --have--;

Column 1, line 21, after "is" insert --such--;

Column 1, line 24, after "use" delete --,--;

Column 1, line 29, delete "the" (second occurrence) and insert --a--;

Column 1, line 31, after "often" insert --is--;

Column 1, line 32, after "is" insert --,-- and after "accordingly" insert --,--;

Column 1, line 35, after "ester" insert --s--;

Column 1, line 37, after "cosmetics" delete "," and after "and" insert --as--;

Column 1, line 43, after "or" insert --as--;

Column 1, line 50, after "of" insert --a--;

Column 1, line 54, after "then" delete ",";

Column 1, line 59, after "of" insert --a--;

Column 1, line 60, after "and" insert --,-- and delete "an" and insert --the--;

Column 1, line 61, after "of" insert --a--;

Column 1, line 63, after "of" insert --a--;

Column 1, line 68, after "of" insert --a-:

Column 2, line 13, delete "the" (second occurrence) and insert --a--;

Column 2, line 14, delete "and";

Column 2, line 16, delete "the";

UNITED STATES PATENT AND TRADEMARK OFFICE
CERTIFICATE OF CORRECTION

PATENT NO. : 5,767,058
DATED : June 16, 1998
INVENTOR(S) : Watanabe, Yuko, et. al.

It is certified that error appears in the above-identified patent and that said Letters Patent is hereby corrected as shown below:

Column 2, line 26, after "and" insert --an-- and after "with" insert --a--;

Column 2, line 31, delete "an";

Column 2, line 34, after "and" insert --a--;

Column 2, line 36, before "long" insert --a--;

Column 2, line 42, after "of" insert --a--;

Column 2, line 50, after "of" insert --the--;

Column 3, line 3, before "combination" insert --a-- and delete "or" (first occurrence) and insert --of--;

Column 3, line 4, after "of" (first occurrence) insert --a--;

Column 3, line 5, after "preferably" insert --a reaction product of the carboxylic acid represented by the formula:

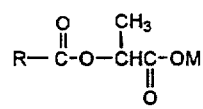

and a basic substance, i.e., --;

UNITED STATES PATENT AND TRADEMARK OFFICE
CERTIFICATE OF CORRECTION

PATENT NO. : 5,767,058
DATED : June 16, 1998
INVENTOR(S) : Watanabe, Yuko, et. al.

It is certified that error appears in the above-identified patent and that said Letters Patent is hereby corrected as shown below:

Column 3, line 17, after "group" insert --derived from the basic substance--;

Column 3, line 18, after "of" insert --the--;

Column 3, line 21, after "both" insert --the--;

Column 3, line 22, after "of" insert --a--;

Column 3, line 26, delete "in" and insert --by--;

Column 3, line 32, before "U.S." insert --see--;

Column 3, line 39, after "of" (first occurrence) insert --a--;

Column 3, line 47, before "except" insert --(--;

Column 3, line 47, after "solvent:" insert --)--;

Column 3, line 49, delete "but";

Column 3, line 54, after "of" insert --a--;

Column 3, line 59, after "of" insert --a--;

Column 4, line 3, after "phases" insert --from--;

Column 4, line 7, after "until" insert --the--;

Column 4, line 21, after "exhibits" insert --a--;

Column 4, line 22, before "generally" insert --(--;

Column 4, line 23, after "phase" insert --)--;

Column 4, line 33, after "of" insert --a--;

Column 4, line 40, delete "in other words" and insert --i.e.--;

Column 4, line 43, after "of" (first occurrence) insert --the--;

Column 4, line 44, delete "the" and insert --a--;

Column 4, line 58, delete "is" and insert --are--;

Column 4, line 61, after "only" insert --does--;

Column 4, line 61, delete "increases" insert --increase--;

Column 4, line 64, after "of" and insert --a--;

Column 4, line 67, after "of" (first occurrence) insert --a--;

UNITED STATES PATENT AND TRADEMARK OFFICE
CERTIFICATE OF CORRECTION

PATENT NO. : 5,767,058
DATED : June 16, 1998
INVENTOR(S) : Watanabe, Yuko, et. al.

It is certified that error appears in the above-identified patent and that said Letters Patent is hereby corrected as shown below:

Column 5, line 4, after "sodium," insert --and--;

Column 5, line 12, after "atoms" insert --,--;

Column 5, line 13, after "cases," insert --a--;

Column 5, line 20, after "in" insert --a--;

Column 5, line 21, delete "suited" and insert --suitable--;

Column 5, line 22, after "use" insert --a--;

Column 5, line 30, delete "the" and insert --a--;

Column 5, line 32, after "of" (first occurrence) insert --a--;

Column 5, line 38, after "of" (first occurrence) insert --a--;

Column 5, line 42, after "of" (first occurrence) insert --a--;

Column 5, line 52, delete "scales" and insert --scale-- and delete "the (second occurrence);

Column 5, line 53, delete "but" and insert --and--;

Column 5, line 58, after "tartrate" insert --s--;

Column 5, line 64, after "condensate" insert --s--;

Column 5, line 65, after "zeolite" insert --s--;

Column 5, line 67, after "tartrate" insert --s--;

UNITED STATES PATENT AND TRADEMARK OFFICE
CERTIFICATE OF CORRECTION

PATENT NO. : 5,767,058
DATED : June 16, 1998
INVENTOR(S) : Watanabe, Yuko, et. al.

It is certified that error appears in the above-identified patent and that said Letters Patent is hereby corrected as shown below:

Column 6, line 2, after "of" insert --a--;

Column 6, line 5, before "alcohol" insert -- an --;

Column 6, line 9, after "weight" insert -- , --;

Column 6, line 17, after "as" insert -- a --;

Column 6, line 35, after "for" (first occurrence) insert -- the--;

Column 6, line 38, after "of" insert -- a --;

Column 6, line 48, delete "weak" and insert -- weakly--;

Column 6, line 53, after "as" insert -- a --;

Column 6, line 55, delete "in" (first occurrence), after "should" insert --, --;

Column 6, line 56, after "however" insert -- , --;

Column 6, line 59, after "matter" insert --of the invention--;

Column 6, line 64, after "of" (first occurrence) insert -- a--;

Column 6, line 65, delete "esters" and insert --ester--;

Column 7, line 1, after "of" insert --the--;

Column 7, line 3, after "of" (first occurrence) insert -- a--;

Column 10, line 59 thereof, between "80" and "%" insert --mol--.

Column 11, line 12, after "of" (first occurrence) insert --the--.

Column 11, line 17, after "of" (first occurrence) insert --the--.

Column 11, line 33, after "of" (second occurrence) insert --the--.

Column 11, line 37, after "of" (second occurrence) insert --the--.

UNITED STATES PATENT AND TRADEMARK OFFICE
CERTIFICATE OF CORRECTION

PATENT NO. : 5,767,058
DATED : June 16, 1998
INVENTOR(S) : Watanabe, Yuko, et. al.

It is certified that error appears in the above-identified patent and that said Letters Patent is hereby corrected as shown below:

Column 12, line 4, after "of" (first occurrence) insert --the--.

Column 12, line 16, after "of" (first occurrence) insert --the--.

Column 12, line 30, after "detergent" insert --composition--.

Column 12, line 33, delete "tartrate" insert --tartrates--.

Please add the following new claims:

--24. The detergent composition according to claim 1, wherein the salt of the long chain carboxylic acid ester of lactic acid has a purity of at least 90 mol%.

25. The detergent composition according to claim 1, wherein the salt of the long chain carboxylic acid ester of lactic acid has a purity of at least 95 mol%.--

Signed and Sealed this

Second Day of May, 2000

*Attest:*

Q. TODD DICKINSON

*Attesting Officer*     *Director of Patents and Trademarks*